United States Patent [19]
Mathis

[11] Patent Number: 6,036,668
[45] Date of Patent: Mar. 14, 2000

[54] PROCESS AND DEVICE FOR THE CONVEYANCE AND MEASURING OF MEDICAL LIQUIDS

[75] Inventor: Jean-Francois Mathis, Saint Gyr en Bourg, France

[73] Assignee: Fresenius AG, Bad Homburg, Germany

[21] Appl. No.: 08/682,519

[22] PCT Filed: Jan. 25, 1995

[86] PCT No.: PCT/EP95/00261

§ 371 Date: Nov. 13, 1996

§ 102(e) Date: Nov. 13, 1996

[87] PCT Pub. No.: WO95/19932

PCT Pub. Date: Jul. 27, 1995

[30] Foreign Application Priority Data

Jan. 25, 1994 [FR] France .................................. 94/00771

[51] Int. Cl.[7] ..................................................... A61M 1/00
[52] U.S. Cl. .............................................................. 604/29
[58] Field of Search ................................. 604/29, 30–34, 604/49, 65–67; 128/DIG. 12, 13

[56] References Cited

U.S. PATENT DOCUMENTS

H1204    7/1993    Sungaila .

| | | |
|---|---|---|
| 1,460,389 | 7/1923 | Mauclère . |
| 3,955,574 | 5/1976 | Rubinstein . |
| 4,167,874 | 9/1979 | Grant . |
| 4,189,943 | 2/1980 | Faure . |

FOREIGN PATENT DOCUMENTS

| | | |
|---|---|---|
| 0105845 | 4/1984 | European Pat. Off. . |
| 614298 | 5/1935 | Germany . |
| WO 89/03696 | 5/1989 | WIPO . |
| WO 92/05406 | 4/1992 | WIPO . |

*Primary Examiner*—John D. Yasko
*Assistant Examiner*—Manual Mendez
*Attorney, Agent, or Firm*—Akin, Gump, Strauss, Hauer & Feld, L.L.P.

[57] ABSTRACT

The invention concerns a process and a device for the combined conveyance and volume measuring of liquids. The conveyance is performed by imparting an overpressure or, respectively, a negative pressure to the liquid by means of a pressurized or depressurized gas cushion. A piston movable in a cylinder which is connected with a receiver containing the liquid exerts either a constant overpressure upon a gas cushion above the liquid to drive the liquid through a line connected with the receiver, or it exerts a constant negative pressure upon the gas cushion to draw the liquid from the line into the receiver. The transported volumes of the liquid are determined by the volumina covered by the piston in the course of its displacements in the cylinder.

18 Claims, 3 Drawing Sheets

PROCESS AND DEVICE FOR THE CONVEYANCE AND MEASURING OF MEDICAL LIQUIDS

BACKGROUND OF THE INVENTION

The present invention concerns a process and a device for the conveyance and measuring of liquids. The invention also concerns the use of the said process and the said device for the conveyance and measuring of medical liquids and in particular of aseptic or contaminated liquids in a peritoneal dialysis system.

It is just the medical employment which, above all, will be referred to in the following but, for a person skilled in the art, it will become clear that the invention will be applicable to the conveyance and measuring of any whatsoever liquid.

It is known that peritoneal dialysis is a technique for the treatment of chronic renal failure which utilizes the peritoneum as a filtration membrane and the exchange between the blood irrigating the said peritoneum and liquid introduced in the abdominal cavity of the patient by means of a catheter. For each cycle, there must be known exactly the volume of the introduced dialysis solution (aseptic liquid, named dialysate) and, likewise, it must be known the volume removed at the end of each cycle (eventually contaminated liquid) in order to be in the condition to judge the quality of the executed dialysis by calculating the obtained ultrafiltration volume. As is generally known, ultrafiltration is the difference between the volumes of the drained dialysate and the introduced dialysate and corresponds to the volume of water removed from the patient. Ultrafiltration is one of the objects of the dialysis and it must be determined precisely and reproducibly.

It is evident in the art, that for the purpose of a precise and reproducible balancing of the volumina of the conveyed liquids, usually employed peristaltic pumps are only applicable in a qualified sense.

In WO-A 89/03 696, a blood purification apparatus for extracorporeal dialysis is described which comprises means for withdrawing blood from a patient into a blood conduit, a blood purification module in fluid flow communication with the said conduit, a blood reservoir for receiving blood from the said module and means for returning blood from the said reservoir to the patient via the blood purification module. The blood flow is actuated by a pump assembly which includes a piston movable in a cylinder. The cylinder is subdivided into a first and a second pump chamber which are separated one from another by a flexible wall. The piston acts in the first pump chamber a hydraulic fluid to distend or relax said flexible wall. In a second chamber, a resiliently walled blood reservoir is provided so that, when the piston acts upon the hydraulic fluid in the first chamber, the flexible separation wall distends and exerts a sufficient squeezing action on said resiliently walled blood reservoir in order to overcome the resistance of the blood circuit, to return the blood to the patient. As the piston retracts, blood flows into the resiliently walled blood reservoir as a result of the negative pressure exerted upon the hydraulic fluid in the first chamber.

Another embodiment for the pump assembly in extracorporeal dialysis is disclosed in EP-A 0 105 845. Therein, the pump assembly consists of a pumping apparatus associated to a pneumatic machine. Said pneumatic machine comprises a rigid housing dividing the cavity into two separated chambers, one connected to the dialyzer and the other connected to the pneumatic machine. The pressure or vacuum created in the other chamber by the pneumatic machine, deflects alternatively the resilient membrane in and out of this chamber causing the volume of the one chamber to vary, thus causing the one chamber to pump the blood in and out of the patient to and from the dialyzer.

However, by the interconnection of such a resilient wall or resilient membrane, a constant pressure upon the liquid on the respective gas cushion cannot be obtained since the actual force and hence the pressure exerted upon the liquid or gas cushion will depend from the actual stretch of the resilient wall or membrane, that is to say, isobaric conditions are not reached.

BRIEF SUMMARY OF THE INVENTION

Therefore, it is an object of the present invention to provide a process and a device for the conveyance of a liquid from at least one receiver in the direction of at least one receptacle and vice versa, said process and device being likewise suitable for the precise measuring of the volumina of the conveyed liquids. In particular, it is an object of the present invention to provide a process and a device that can be utilized in a technique such as peritonea dialysis, which allows the transport of the dialysis solution in the abdominal cavity of the patient and to remove therefrom the used dialysate in quantities precisely measured.

According to the invention, there is provided a process for the conveyance and measuring of a liquid running in a conveyance assembly from at least one receiver in the direction of at least one receptacle and vice versa, the conveyance being effected by a drive assembly connected with the conveyance assembly by providing a positive or negative pressure upon a gas cushion in the reservoir, said process being characterized in that both, the conveyance assembly and the drive assembly are actuated by a control and signal unit and the drive assembly is composed of at least one cylinder having a movable piston and driving means suitable to controllably operate the movement of said piston in said cylinder such that it exerts either an isobaric positive or negative pressure and in that the, volumina of the liquids transported in the conveyance assembly are measured in the drive assembly by determining the volumina that have been covered by the piston in the course of its displacements in the cylinder.

According to the present invention, there is further provided a device for the conveyance of a liquid via a line from at least one receiver into the direction of a receptacle or vice versa as well as for the measuring of the volumina, of the conveyed liquids, said device comprising a drive assembly and a conveyance assembly containing said reservoir and connected by a connection line to the drive assembly, said device being characterized in that the conveyance assembly and the drive assembly are connected with a control and signal unit, the drive assembly comprises at least one cylinder having a movable piston and being associated with driving means suitable to controllably operate the movement of said piston in the cylinder so as to impart a constant positive or negative pressure to a gas cushion, said driving means being associated with measuring means for the measuring of the displacement of the piston in the cylinder and the transported volumina.

Consequently, according to the invention, the volume of the gas cushion, e.g. of air, which is pressurized or depressurized by a piston serves as driving means in order to operate the regulated transfer of the liquid. When the process and the device according to the invention are applied in that the displacement of the piston in the cylinder is measured, it is possible to measure the transported volumina of the liquids or in case of peritoneal dialysis the aseptic liquid and/or of the contaminated liquid with great precision.

Advantageously, the device should contain two different receivers, each being connected with the same receptacle and with the same cylinder via different lines, equipped with controlled obturators, in order to allow the receptacle to be -filled with liquid from one of said receivers and to lead the liquid from the receptacle towards the second receiver, without contaminating the first receiver with the liquid coming from the receptacle.

The above-described process or the devices may be suitably utilized in the field of peritoneal dialysis technique for the conveyance of a controlled amount of an aseptic dialysis solution from a first receiver to the abdominal cavity of the patient and to discharge the used dialysis solution coming from the said cavity into the second receiver.

For the introduction of the aseptic dialysis solution and for the removal of the effluent contaminated dialysate, two intermediate receivers or "burettes" are utilized which are connected with the catheter of the patient. The burette for the feeding dialysis solution is itself connected with a main reservoir of dialysis solution which allows to fill the said burette, whereas the burette destined for the evacuation of effluent liquid is connected with a discarding system. Naturally, the connection lines are, equipped with means for controlled closing of whatsoever type, but generally, they are made of simple clips called "electro-clamps" which laterally compress a flexible conduit in order to prevent the liquid from passing.

When the process and the device according to the invention are applied in that the displacement of the piston in the cylinder is measured, it is possible to measure the transported volumes of the medical liquids or in case of peritoneal dialysis the aseptic liquid and/or of the contaminated liquid with great precision.

If required, a sterile filter may be interposed between the circuit of the liquid to be transported and the driving gas, in order to prevent any contamination of the liquid by the gas.

BRIEF DESCRIPTION OF VARIOUS VIEW OF THE DRAWINGS

The application of the invention is illustrated in the annexed key plans, in which.

DETAILED DESCRIPTION OF THE INVENTION

Figure 1:
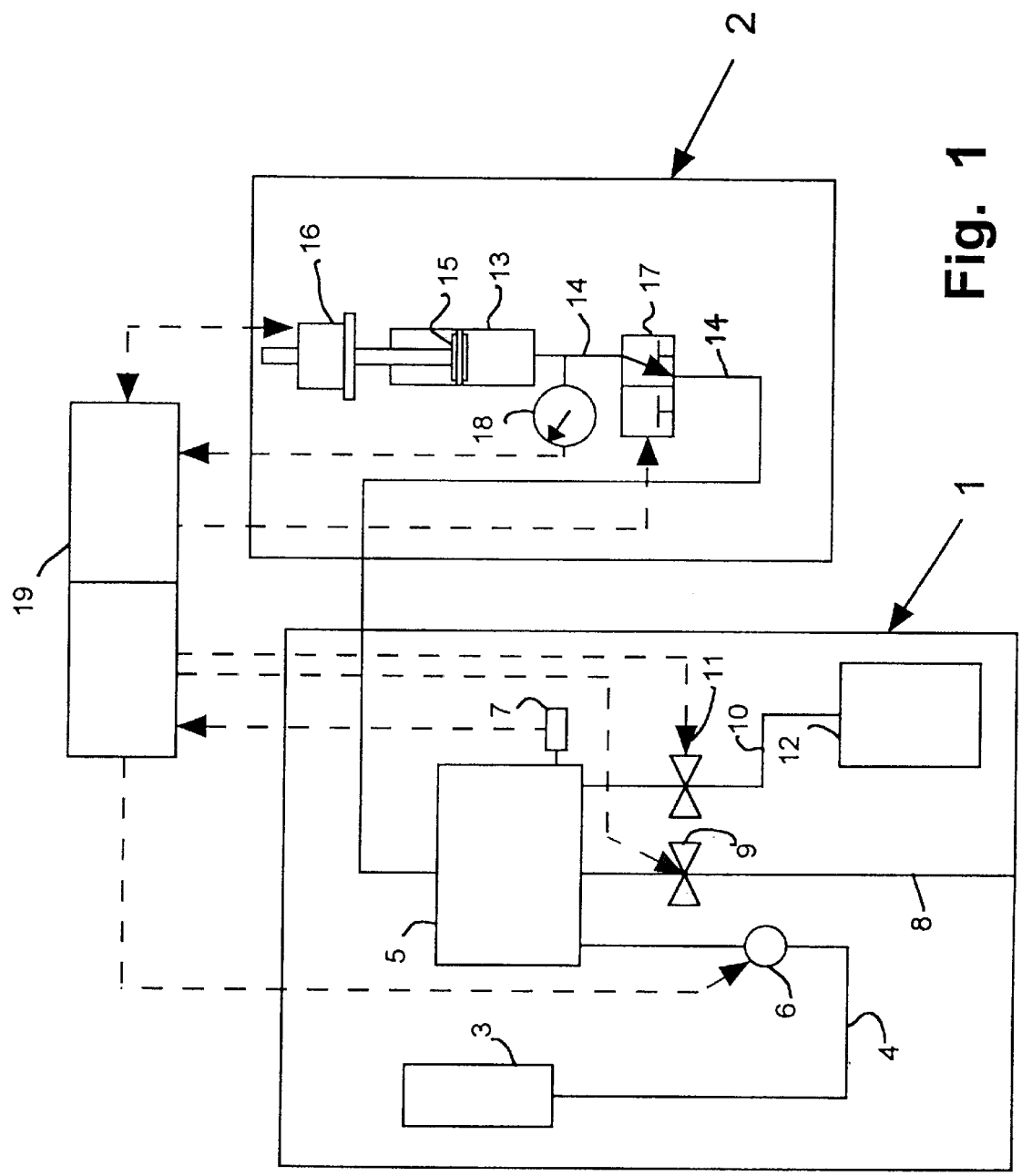
FIG. 1 is an elementary diagram illustrating the inventive process in an application of the conveyance of medical liquids.

First, reference is made to FIG. 1.

In said figure, the assembly for the conveyance of the medical liquids is designated by reference numeral 1 and the drive and measuring assembly according to the invention by reference numeral 2.

In a device destined to feed a patient with a medical liquid, e.g. with an infusion, the assembly 1 comprises a reservoir 3 for the medical liquid, that is connected via line 4 with an intermediate receiver 5 or "burette" through a supply means, such as a pump 6, which starts operating when a level generator 7 signals to the control and signal unit 19 that a predetermined minimum level has been reached in the burette 5. In case of a transfusion, the reservoir 3 is replaced by a blood donor. A line 8 equipped with an obturator 9, such as an Uelectro-clamp", connects the reservoir 5 with the catheter connected with the patient.

According to the invention, a cylinder 13 containing a gas, e.g. air, is connected through line 14 with the upper portion of the burette 5, where line 14 ends above the surface of the medical liquid contained therein. In cylinder 13, there is displaced a piston 15 controlled by a linear stepping motor 16. In line 14, a three-way distributor 17 is interposed. A pressure sensor 18 is placed in parallel to said line 14.

In a device destined to take also a medical liquid from a patient, e.g. with peritoneal dialysis, a line 10, likewise equipped with an obturator 11, such as an "electro clamp" is connected with a drainage system 12. In case of single dialysis, said drainage system 12 is replaced by a dialyzer.

Under the effect of an overpressure or a negative pressure exercised by the piston 15, the volume of the gas cushion between the piston and the medical liquid contained in the burette 5 serves as driving agent, in order to control the displacement of the medical liquid in line 8 towards the patient or the discharge of the medical liquid coming from the patient through line 10. The position of the piston 15 in the cylinder 13 can be continuously measured by the deduction of the number of excursions or partial excursions accomplished by the motor 16.

The position of the piston 15 acts in the cylinder 13 over a volume that is greater than the one of the burette 5, and in operation, its initial position is about in the middle of the cylinder. Since the pressure sensor 18 signals the actual pressure in the cylinder 13 to the control and signal unit 19 which consequently regulates the stepping motor 16, the position of the piston is controlled by the pressure in the cylinder so as to maintain this pressure more or less constant, that is to say, isobaric conditions are maintained. If the pressure in the cylinder is greater than the one of the connected circuit, e.g. of line 8, the liquid contained in the said circuit is expelled. If this pressure is lower than the one of the connected circuit, the liquid is sucked in, in order to fill the said circuit. In line 4, a simple obturator, such as an "electro-clamp" may replace the pump 6 and, after having obturated components 9 and 11 which are under control of unit 19, the receiver 5 may be easily filled from the reservoir 3 by judiciously changing the position of the piston 15 in the cylinder 13.

The dimensions of the connection lines are adjusted so as to obtain only minor pressure drops at the utilized rates, and hence, a pressure equilibrium will appear from end to end, whereas the compressibility of the air does not affect the precision of the measurement of the volume. In any case, the pressure is measured when the liquids are unmoved in order to grant an exact calculation of the transferred volume. Furthermore, when an overpressure or a negative pressure is imparted to the concerned volumes, the control system of the assembly can take the development of significant parameters into account, in particular the temperature of the air.

As can be seen in the following, when applied in a process destined, inter alia, for volume balancing such as, e.g., in peritoneal dialysis, two different receivers or "burettes" are utilized, one for the aseptic dialysis solution and the other for the contaminated dialysis solution, but for other applications, such as infusion, transfusion, dialysis or urine measuring, only one single intermediate receiver may be utilized.

Figure 2:
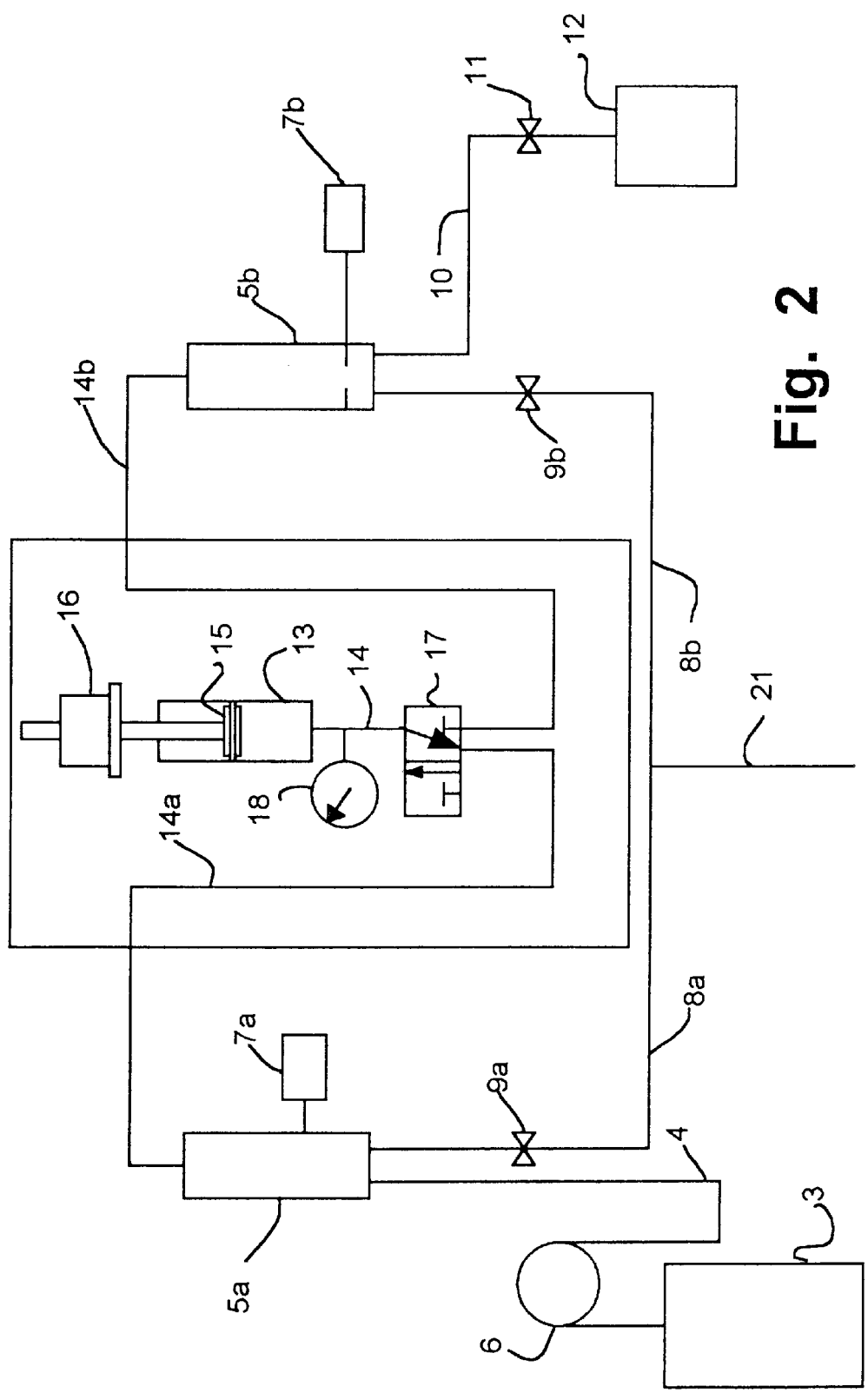
FIGS. 2 and 3 are diagrams of two embodiments of the device according to the invention, as represented in an application for peritoneal dialysis;.
Figure 3:
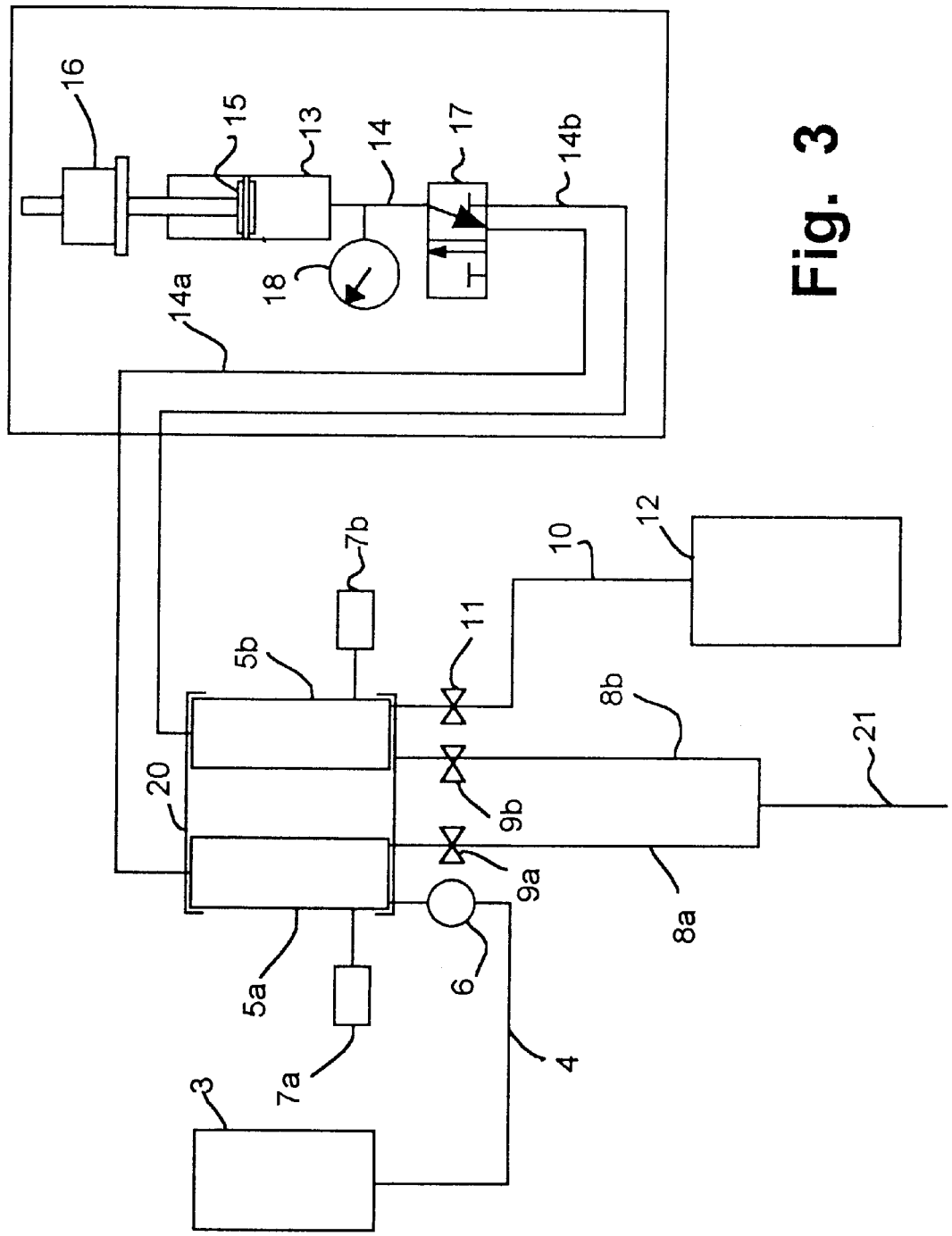

FIGS. 2 and 3 represent two embodiments of the device according to the invention when applied in peritoneal dialysis. Those components already described in FIG. 1 are designed by the same reference numerals. In both cases, two burettes 5a, 5b are utilized, each equipped with a controlled obturator 9a, 9b and each connected via line 8a, 8b with line 21, which is itself connected with the catheter of the patient.

In case of FIG. 3, the burettes 5a–5b are aggregated in a support unit 20, while in FIG. 2, they are separated. As described above, the burette 5a is connected with the reservoir 3 via line 4 and the burette 5b with the drainage system 12 via line 10. Two distinct paths of the distributor 17 are each connected via lines 14a and 14b respectively with the upper portion of the burette 5a, 5b so that an overpressure or a negative pressure can be equally imparted on the liquids contained in each of said paths by an appropriate change of the position of the piston 15 in the cylinder 13. Each of the burettes 5a, 5b is equipped with a level detector 7a, 7b.

By analogy with the corresponding elements of FIG. 1, the elements with reference numerals 6, 7a, 7b, 9a, 9b, 11 and 16–18 are likewise connected with the control unit 19 (not shown).

Said two devices work as follows. In order to effect the initial filling of the assembly with dialysis solution, the "electroclamps" 9a, 9b and I 1 are opened. Line 19 of the patient is not yet connected but it is only held up above the machine, in order to prevent the discharge of the dialysis solution. The distributor 17 is connected with cylinder 13 via line 14a.

The pump 6 is set in motion and the system is filled until the predetermined minimum level of the entry burette 5a is reached. Electro-clamp 11 is closed and thereupon, filling is continued by changing the position of the piston in order to raise the pressure and to fill line 21 of the patient and exit burette 5b up to a determined minimum level. Electroclamps 9a and 9b are closed and line 10 is connected with the catheter of the patient. The position of piston 15 is changed in order to obtain a zero pressure in entry burette 5a. The distributor 17 is thrown over in order to connect cylinder 13 with line 14b and hence, the pressure in exit burette 5b vanishes. At that time, there exist the initial conditions in order to execute any operation of filling, rinsing or beginning with the cycle.

In order to inject the dialysis solution into the patient, the pump is set in motion to fill the burette 5a, while the electro-clamps 9a, 9b and 11 are closed and the cylinder 13 is connected with the distributor 17 via line 14a. The pressure in burette 5a is kept constant by changing the position of piston 15. Thus, the volume of the dialysis solution introduced into burette 5a can be measured.

At a stop of the pump 6 at a desired volume, pressure is imparted to burette 5a by changing the position of the piston 15 and opening the electro-clamp 9a. By changing the position of the piston 15, pressure is kept constant until the end of the transport of the dialysis liquid. In order to realize a permanent pressure equilibrium, the change of the position of the piston must be performed sufficiently slow. When the unitary volume for the injection is reached, the piston is stopped. In consideration of the volume of the burette 5a, the cycle can be repeated as often as necessary to obtain a predetermined injection volume.

To proceed with the drainage, cylinder 13 is connected with line 14b and a negative pressure of about 100 mbar is imparted by changing the position of the piston 15. The electro-clamp 9b is opened and, by changing the position of the piston, the negative pressure is maintained until the volume of the burette or the maximum time of drainage is obtained. Then the electro-clamp 9b is closed and, after having opened the electro-clamp 11, the burette is pressurized by the change of the position of the piston. The position of the piston 15 is changed at a constant pression to a volume that corresponds to the volume of the burette 5b, whereupon the electro-clamp I 1 is closed. The cycle is resumed until the equilibrium of the pressures in the course of the drainage lasts without change of the position of the piston during an appointed time.

The device according to the invention is suitable for embodiments of minor dimensions, that are perfectly compatible with existing devices for peritonea dialysis.

Therefore, e.g. the piston 15 should have a diameter of 40 mm, which corresponds to a cross-section of 12.5 cm' for the change of the position of the piston of 0.8 mm for a moved air volume of 0.8 ml. When utilizing usual burettes having a volume of 150 ml, the emptying or filling of a burette would correspond to a stroke of the piston of 120 nun, which is to be multiplied by 1.2 in. order to take pressurizing into consideration which corresponds in practice to a stroke of about 150 nun.

For an overpressure or a negative pressure of 200 mbar, the force to be exercised disregarding the friction amounts to 25 N. In practice, the total effort to be exercised will be in the order of magnitude of 35 N.

The linear actuating device 16 ensures a displacement of the piston of 0.0254 mm per step of the control stepping motor, that is to say a volume of air or liquid is displaced by 0.03 ml per step. The speed of the displacement amounts to 300 steps per second, that is to say 9.57 ml/s or 574 ml/min.

The pressure must not be taken into consideration insofar as it can be maintained constant during the entire displacement of the piston, without leakage to the outside.

The pressure sensors associated to an analogue to digital converter allow to maintain a sensitivity better than 0. I mbar which, for a volume of 200 ml, corresponds to a variation of 0.02 ml.

However, it is possible to measure with a precision that equals at least 0.1% of the volumes of 150 ml, corresponding to the volumes of usual burettes.

Additionally to each receiver may be attributed a separate drive and measuring assembly.

Hence, the invention provides a simple and very precise means for the assistance of usual devices for the conveyance and measuring of medical liquids in fields of application, such as infusion, transfusion, determination of urine, dialysis and peritoneal dialysis.

I claim:

1. A process for the conveyance and measuring of a liquid running in a conveyance assembly (1) from at least one receiver (5) included in said conveyance assembly (1) in the direction of at least one receptacle external to the conveyance assembly (1) and vice versa, the conveyance being effected by a drive assembly (2) connected to said conveyance assembly (1) by providing a positive or negative pressure upon a gas cushion in said at least one receiver (5) above the liquid to be conveyed, wherein said conveyance assembly (1) and said drive assembly (2) are actuated by a control and signal unit (19) and said drive assembly (2) is composed of at least one cylinder (13) having a movable piston (15) and driving means (16) suitable to controllably operate the movement of said piston (15) in said cylinder (13) such that it exerts either an isobaric positive or negative pressure and wherein the volume of the liquid transported into said conveyance assembly (1) is measured in said drive assembly (2) by determining the volumina that have been covered by said piston (15) in the course of its displacements in said cylinder (13).

2. A device for the conveyance of a liquid via a line from at least one receiver (5) in the direction of at least one receptacle or vice versa as well as for measuring the volumina of the conveyed liquids, said device comprising a drive assembly (2) connected by at least one connection line (14) to a conveyance assembly (1) and said at least one connection line 14 ends in said at least one receiver (5) that is included in said conveyance assembly (1), said drive assembly (2) including a pneumatic machine for imparting via said at least one connection line (14) a positive pressure or a negative pressure to a gas cushion in said at least one receiver (5) above the liquid to be conveyed, wherein said conveyance assembly (1) and said drive assembly (2) are connected to a control and signal unit (19), said drive assembly (2) comprising at least one cylinder (13) having a movable piston (15) that is associated with driving means (16) suitable to controllably operate the movement of said piston (15) in the cylinder (13) so as to impart a constant positive or negative pressure to a gas cushion, and said driving means (16) being associated with a measuring means for the determination of the displacement of said piston (15) in said cylinder (13) and the transported volumina.

3. A device according to claim 2, characterized in that the drive means which sets the piston (15) in action is a linear stepping motor (16).

4. A device according to claim 2, characterized in that the receiver (5) is controllably connected on the one hand with a supply reservoir (3) of a liquid and on the other hand with draining means (12).

5. A device according to one of claim 2, characterized in that the receiver (5) is connected on the one hand with a supply reservoir (3) of a medical liquid or with a blood donor and on the other hand via line (8) with a catheter of a patient.

6. A device according to claim 2, characterized in that the receiver (5) is connected on the one hand with a catheter of a patient via line (8) and on the other hand via line (10) with a drainage system (12) or a dialyser.

7. A device according to claim 2, characterized in that it comprises two receivers (5a,5b) separately connected with the receptacle, wherein each of said receivers can furthermore be selectively connected with the cylinder (13) by means of connection lines (14a,14b) and a means (17) for the junction of said lines that is interposed between the receivers (5a,5b) and the cylinder (13).

8. A device according to claim 2, characterized in that it comprises two receivers (5a,5b) separately connected with separately associated cylinders by means of connection lines and means for the junction of said lines that are interposed between the receivers and their associated cylinder.

9. A device according to claim 7, characterized in that one (5a) of said receivers is connected with a reservoir (3) of a liquid and the other (5b) with a draining means (12).

10. Use of the process according to claim 1 for the conveyance of an aseptic dialysis solution in controlled quantities from a first receiver (5a) to the abdominal cavity of a patient and for draining the used dialysis solution coming from said cavity up to a second receiver (5b).

11. Use of the process according to claim 1 for the measuring of the conveyed medical liquids in an operation of infusion or transfusion.

12. Use of the process according to claim 1 for the measuring of the conveyed medical liquids in an operation of dialysis or determination of urine.

13. A device according to claim 3, characterized in that the receiver (5) is controllably connected on the one hand with a supply reservoir (3) of a liquid and on the other hand with draining means (12).

14. A device according to claim 3, characterized in that the receiver (5) is connected on the one hand with a supply reservoir (3) of a medical liquid or with a blood donor and on the other hand via line (8) with a catheter of a patient.

15. A device according to claim 3, characterized in that the receiver (5) is connected on the one hand with a catheter of a patient via line (8) and on the other hand via line (10) with a drainage system (12) or a dialyser.

16. A device according to claim 3, characterized in that it comprises two receivers (5a,5b) separately connected with the receptacle, wherein each of said receivers can furthermore be selectively connected with the cylinder (13) by means of connection lines (14a,14b) and a means (17) for the junction of said lines that is interposed between the receivers (5a,5b) and the cylinder (13).

17. A device according to claim 3, characterized in that it comprises two receivers (5a,5b) separately connected with separately associated cylinders by means of connection lines and means for the junction of said lines that are interposed between the receivers and their associated cylinder.

18. A device according to claim 8, characterized in that one (5a) of said receivers is connected with a reservoir (3) of a liquid and the other (5b) with a draining means (12).

* * * * *